United States Patent
Nitta et al.

(10) Patent No.: US 9,527,792 B2
(45) Date of Patent: Dec. 27, 2016

(54) METHOD FOR PRODUCING (METH)ACRYLIC ACID

(71) Applicant: MITSUBISHI RAYON CO., LTD., Chiyoda-ku (JP)

(72) Inventors: Masanori Nitta, Otake (JP); Toshihiro Satou, Otake (JP); Tomomasa Tatsumi, Otake (JP)

(73) Assignee: MITSUBISHI RAYON CO., LTD., Chiyoda-ku (JP)

( * ) Notice: Subject to any disclaimer, the term of this patent is extended or adjusted under 35 U.S.C. 154(b) by 0 days.

(21) Appl. No.: 15/034,109

(22) PCT Filed: Apr. 27, 2015

(86) PCT No.: PCT/JP2015/062699
§ 371 (c)(1),
(2) Date: May 3, 2016

(87) PCT Pub. No.: WO2015/166911
PCT Pub. Date: Nov. 5, 2015

(65) Prior Publication Data
US 2016/0264504 A1 Sep. 15, 2016

(30) Foreign Application Priority Data
Apr. 30, 2014 (JP) ................................ 2014-093584

(51) Int. Cl.
*C07C 51/25* (2006.01)
*B01J 27/199* (2006.01)

(52) U.S. Cl.
CPC ............ *C07C 51/252* (2013.01); *B01J 27/199* (2013.01)

(58) Field of Classification Search
CPC .............................. C07C 51/252; B01J 27/199
See application file for complete search history.

(56) References Cited

U.S. PATENT DOCUMENTS 9,174,910 B2 * 11/2015 Nishiguchi ........... C07C 51/235

FOREIGN PATENT DOCUMENTS

| JP | 53-30688 | | 3/1978 |
| JP | 63-216835 A | | 9/1988 |
| JP | 11-130722 A | | 5/1999 |
| JP | 2002-348258 A | | 12/2002 |
| JP | 2003-305367 A | | 12/2002 |
| JP | 2006-218434 A | | 8/2006 |
| JP | 2008-24644 A | | 2/2008 |
| JP | 2010-90116 A | | 4/2010 |
| WO | WO 2009/116550 | * | 9/2009 |
| WO | WO 2012/033048 A1 | | 3/2012 |

OTHER PUBLICATIONS

International Search Report issued Jul. 14, 2015, in PCT/JP2015/062699 filed Apr. 27, 2015.

* cited by examiner

*Primary Examiner* — Shailendra Kumar
(74) *Attorney, Agent, or Firm* — Oblon, McClelland, Maier & Neustadt, L.L.P.

(57) ABSTRACT

The present invention provides a (meth)acrylic acid-producing method capable of suppressing formation of carbides so that the production yield of (meth)acrylic acid is enhanced. In such a method, (meth)acrylic acid is produced through gas-phase catalytic oxidation reactions of (meth)acrolein by using molecular oxygen in a fixed-bed reactor configured to have a packed layer containing a packing material and a catalyst layer formed with a catalyst containing at least molybdenum and vanadium. The packed layer contains a packing material that has been used at least once for above gas-phase catalytic oxidation reactions, and the catalyst is present in the packed layer at 0.001~0.15 mass % of the total amount of the packing material.

12 Claims, 1 Drawing Sheet

METHOD FOR PRODUCING (METH)ACRYLIC ACID

This Application a 371 of PCT/JP2015/062699, filed 2015 Apr. 27.

TECHNICAL FIELD

The present invention relates to a method for producing (meth)acrylic acid.

BACKGROUND ART

Catalysts used industrially for gas-phase catalytic oxidation reactions are generally used for a certain period of time in relation to regular maintenance scheduling of the plant facility or the like. After the time of use has expired, the catalyst is removed from the reaction tube and is replaced with a newly produced catalyst. Catalyst poisoning by impurities contained in the reaction gas and formation of carbides are observed in the removed catalyst and on the reaction tube. Such substances cause a decrease in reaction yields and an increase in the rate of pressure loss during the time of use of the catalyst. Considering such problems, various solutions such as below have been proposed.

Patent Document 1 describes a technology where a treatment agent is arranged above the catalyst layer in a reaction tube or on the upper portion of an upper tube sheet in the reactor so that inhibitors produced in previous reactions are blocked from attaching to the catalyst for subsequent reactions. Patent Document 2 describes a technology where an inert substance layer is arranged by packing an inert substance between the first catalyst layer and the subsequent catalyst layer so that when a reaction gas from previous reactions passes through the inert layer, impurities contained in the reaction gas are removed to prevent deterioration of catalytic activity in the subsequent catalyst layer. Patent Document 3 describes a technology where an inert support coated with a molybdenum compound is used. Such a technology is effective, but cannot yield sufficient reaction results, thus causing an increase in production costs. Accordingly, further improvement is necessary. Patent Document 4 describes using a mixture of a catalyst and an inert substance so that hotspot phenomena are prevented during oxidation reactions and the selectivity of the catalyst and its life are improved. In addition, Patent Document 5 describes a technology where an inert substance or a packing material for a preheating layer is packed near the inlet to the catalyst layer so that the reaction gas is cooled or preheated, and an inert substance is packed near the outlet of the catalyst layer so that the residence time of the gas in an empty space is shortened and consecutive reactions are suppressed.

PRIOR ART DOCUMENT

Patent Document

Patent Document 1: JP2008-24644A
Patent Document 2: JP H11-130722A
Patent Document 3: JP2010-90116A
Patent Document 4: JP S53-030688B
Patent Document 5: JP S63-216835A

SUMMARY OF THE INVENTION

Problems to be Solved by the Invention

However, when (meth)acrylic acids are produced using technologies described in the above patent documents, carbides are formed as byproducts and an insufficient yield of (meth)acrylic acid will result. Accordingly, further improvement is necessary.

The objective of the present invention is to provide a (meth)acrylic acid-producing method capable of suppressing formation of carbides so that the production yield of (meth)acrylic acid is enhanced.

Means for Solving Problems

The present invention relates to a method for producing (meth)acrylic acid through gas-phase catalytic oxidation reactions of (meth)acrolein by using molecular oxygen in a fixed-bed reactor configured to have a packed layer containing a packing material and a catalyst layer formed with a catalyst containing at least molybdenum and vanadium. The packing material includes such a packing material that has been used at least once for above gas-phase catalytic oxidation reactions, and the catalyst is present in the packed layer at 0.001~0.15 mass % of the total amount of the packing material.

Effects of the Invention

According to the present invention, formation of carbides is suppressed and the production yield of (meth)acrylic acid is enhanced.

DESCRIPTION OF THE EMBODIMENTS

An aspect of the present invention is a method for producing (meth)acrylic acid through gas-phase catalytic oxidation reactions of (meth)acrolein by using molecular oxygen in a fixed-bed reactor configured to have a packed layer containing a packing material and a catalyst layer formed with a catalyst containing at least molybdenum and vanadium. The packing material includes such a packing material that has been used at least once for above gas-phase catalytic oxidation reactions, and the catalyst is present in the packed layer at 0.001~0.15 mass % of the total amount of the packing material.

Regarding a packing material that has been used at least once for above gas-phase catalytic oxidation reactions and that is used again in a packed layer, the inventors have studied the life of a catalyst to see if reaction results of the catalyst are enhanced when a packing material with attached catalytic components is used for the packed layer. They have found the following: if the amount of a catalyst relative to the total amount of the packing material in a packed layer (hereinafter may also be referred to as the rate of contained catalyst) exceeds 0.15 mass %, the reaction result is lower than that when the rate of contained catalyst is 0.15 mass % or less, and when the rate of contained catalyst exceeds 0.15 mass %, carbides are formed and the catalytic activity is lowered; on the other hand, if the rate of contained catalyst is within a range of 0.001~0.15 mass %, the presence of a catalyst at such a rate suppresses formation of carbides to be attached to the catalyst and to the reaction tube, and the reaction result is thereby enhanced. Accordingly, the present invention is completed.

It is not clear why the presence of a catalyst in a packed layer suppresses the formation of carbides to be attached to the catalyst and the reaction tube. However, when a trace amount of carbide precursors contained in a source gas makes contact with a proper amount of the catalyst in a packed layer, it is thought that formation of carbides in a subsequent catalyst layer is suppressed. Here, when the rate of contained catalyst is less than 0.001 mass %, cleaning costs also increase as described later.

Considering cleaning costs and further improvement of the production yield of (meth)acrylic acid achieved by suppressing the formation of carbides, the rate of contained catalyst is preferred to be 0.001~0.1 mass %, more preferably 0.001~0.05 mass %. During the packing process, the catalyst may be powdered or cracked and may migrate into the gaps in the packing material of the packed layer. The catalyst contained in the packed layer is effective in suppressing the formation of carbides regardless of whether or not it is attached to the packing material. Therefore, when the rate of contained catalyst is calculated, the mass of the catalyst is the total mass contained in the packed layer regardless of its state, including the amount of catalyst that has migrated into the packed layer and located in the gaps of the packing material. In addition, the "total amount of the packing material" indicates the total mass of the packing material that excludes the attached catalyst. Also, when there is no catalyst present in the gaps of a packing material and when a packing material with attached catalyst and another packing material without attached catalyst are mixed together to be used, the rate of contained catalyst is shown as the average value. Namely, the rate of contained catalyst in such a case is the rate of catalyst attached to the packing material relative to the total amount of the packing material in the mixture.

The catalyst present in the gaps of a packing material is effective in suppressing the formation of carbides; however, such a catalyst also causes an increase in the rate of pressure loss by blocking the passage of the reaction gas. Thus, it is preferred to use a catalyst that is not powdered or is unlikely to be powdered. In addition, when a catalyst is packed, it is preferred to supply air from the bottom of the reaction tube so as to work as a cushion during the packing process to prevent a catalyst from being powdered, or to use a catalyst and a packing material that are packed in bags. Packing a catalyst and a packing material in bags is preferable. When no catalyst is present in the gaps of a packing material, only the amount of the catalyst attached to the packing material is used to calculate the rate of contained catalyst.

To the packing material in a packed layer, a catalyst is preferred to be attached at 0.001~0.1 mass %, more preferably 0.001~0.05 mass %, of the total amount of the packing material.

The packing material in a packed layer includes a packing material used at least once for above gas-phase catalytic oxidation reactions. If a new, namely, unused packing material is always used as the packing material in a packed layer, production costs and the amount of waste product will increase. Thus, the packing material in the packed layer is removed along with the catalyst after the completion of reactions and then separated from the catalyst so as to be used again while filling unused packing material in place of the amount lost during repeated packing and removal or the amount discarded due to cracking, deformation and the like.

When a used packing material is used for a packed layer, later-described cleaning is conducted on the used packing material with attached catalyst so that it is easier to set the rate of contained catalyst to be within the above range. The catalyst attached to the used packing material is either the catalyst in use or a used catalyst. As for a packing material related to the present invention, it is an option to use either an unused packing material with attached unused catalyst or an unused packing material without attached catalyst mixed with a used packing material.

The amount of used packing material in a packed layer is not limited specifically as long as the rate of contained catalyst is within a range of 0.001~0.15 mass %, but it is preferred to be 80 mass % or more, more preferably 90 mass % or more. It is even more preferable if the packing material in a packed layer is 100 mass %, namely, entirely used packing material.

The used packing material is preferred to have been used at least once for above gas-phase catalytic oxidation reactions and cleaned subsequently. By cleaning a used packing material having an excess amount of catalyst attached after gas-phase catalytic oxidation reactions, the rate of contained catalyst is easily set to be within the above range.

The inventors have found that the catalyst attached to a packing material is easily removed by using a cleaning solution capable of dissolving the catalytic component. The cleaning solution is not limited specifically; any type capable of dissolving the attached catalyst may be used unless it negatively affects the catalyst and packing material. Such a cleaning solution is preferred to be tap water, deionized water (hereinafter may also be referred to as DI water), alkaline solutions or the like. From the viewpoint of excellent cleaning performance, deionized water and 1~5 mass % ammonia solutions (hereinafter may also be referred to as ammonia water) are more preferable. Considering even higher cleaning performance, it is preferred to soak used packing material in ammonia water and then clean it in deionized water. The amount of attached catalyst decreases when the cleaning duration is set longer. When ammonia water is used, the amount of attached catalyst decreases when the concentration of ammonium is reduced. The method for drying the cleaned packing material is not limited specifically. Air drying, hot blowing and the like may be employed.

Other than a cleaning method using a cleaning solution, mechanical polishing using a brush or a file may also be employed to remove the excess amount of catalyst attached to the surfaces of a packing material after gas-phase oxidation reactions. Polishing is also included in the category of cleaning methods related to the present invention. Such cleaning is conducted to have a resultant rate of contained catalyst at 0.001~0.15 mass % when only the cleaned packing material is used. The amount of attached catalyst decreases by cleaning; however, to clean the packing material until the rate of contained catalyst becomes lower than 0.001 mass %, a significantly longer time is necessary for cleaning while the amount of ammonium increases, and cleaning costs are thereby higher. The cleaned packing material may be mixed with an unused packing material so that the average rate of contained catalyst is set at 0.001~0.15 mass %. In such a case, the mixing rate is not limited specifically as long as the resultant rate of contained catalyst is at 0.001~0.15 mass %. The mixing rate may be selected appropriately so as to balance the cleaning cost, cost of discarding waste products, cost of new packing materials and the like.

In addition, a packing material used at least once for above gas-phase catalytic oxidation reactions may be used without being cleaned. Such a packing material may be used alone for a packed layer as long as the rate of contained catalyst remains within a range of 0.001~0.15 mass %. If the rate of contained catalyst exceeds the above range, a mixture is prepared by mixing an unused packing material without attached catalyst so that the average rate of contained catalyst is set at 0.001~0.15 mass % in the packed layer.

The properties of a packing material in the packed layer are not limited specifically as long as the packing material has heat resistance to a temperature employed for reactions. Packing materials are made of, for example, silica, alumina, silica alumina, magnesia, titania, SUS (stainless steel) and the like. Packing materials are not limited to having any specific shape; for example, spherical, columnar and cylindrical shapes, coil- and sheet-shapes and the like may be used. Alternatively, random packing materials such as Cascade Mini Rings, Tellerettes, Pall Rings, Saddles, and Medal-Paks may also be used. Packing materials are not limited to any specific size, unless the packing materials build bridges when packed in a reaction tube, or the packing material increases the rate of pressure loss. The size is preferred to be approximately the same as that of a catalyst. From economic viewpoints, ceramic balls and coil springs are preferred, and silica-alumina ceramic balls and SUS coil springs are especially preferred. Those packing materials may be used alone or in combination thereof.

In an embodiment of the present invention, a catalyst to be used for producing (meth)acrylic acid is not limited specifically, as long as it contains molybdenum and vanadium. However, using chemical compounds represented by formula (1) below is preferred in order to achieve higher effects of the present invention. The elemental composition of the compound represented by formula (1) is obtained from the initial amount of each material used to prepare the compound.

$$Mo_aP_bCu_cV_dX_eY_fO_g \qquad (1)$$

(In the above formula, Mo, P, Cu, V and O respectively indicate molybdenum, phosphorus, copper, vanadium and oxygen. "X" represents at least one element selected from a group consisting of iron, cobalt, nickel, zinc, magnesium, calcium, strontium, barium, titanium, chromium, tungsten, manganese, silver, boron, silicon, tin, lead, arsenic, antimony, bismuth, niobium, tantalum, zirconium, indium, sulfur, selenium, tellurium, lanthanum and cerium. "Y" represents at least one element selected from a group consisting of potassium, rubidium, cesium and thallium. In addition, "a~g" represent the atomic composition ratio of each element: when "a" is 12, then "b" is set at $0.1 \leq b \leq 3$, "c" is set at $0.01 \leq c \leq 3$, "d" is set at $0.01 \leq d \leq 3$, "e" is set at $0 \leq e \leq 10$, "f" is set at $0.01 \leq f \leq 3$, and "g" is set to have an atomic ratio of oxygen required to satisfy the valence of the total atoms.

The method for preparing a catalyst is not limited specifically in an embodiment of the present invention. Any method may be employed unless it causes significantly uneven distribution of catalytic components. Examples of methods are sedimentation, coprecipitation, impregnation and the like. Examples of materials for preparing a catalyst are nitrates, carbonates, acetates, ammonium salts, oxides and halides; those may be used alone or in combination thereof. In particular, examples of molybdenum are ammonium paramolybdate, molybdenum trioxide, molybdic acid, molybdenum chloride and the like. Examples of phosphorus are orthophosphoric acid, phosphorus pentoxide, ammonium phosphate and the like. Examples of vanadium are ammonium metavanadate, vanadium pentoxide and the like. Those materials may be used alone or in combination thereof.

A catalyst is not limited to any specific shape; for example, it may be a spherical grain, a columnar pellet, a ring shape, a granule crushed into pieces after being molded into a shape or the like. As for the size of a catalyst, its diameter is preferred to be at least 0.1 mm but no greater than 10 mm. When the diameter of a catalyst is set to be at least 0.1 mm, the rate of pressure loss is minimized in the reaction tube. When the diameter is set to be no greater than 10 mm, the catalytic activity is enhanced.

To activate a catalyst, it is preferred to conduct thermal treatment on the catalyst. Conditions of thermal treatment are not limited specifically. To enhance the production yield of (meth)acrylic acid, thermal treatment is preferred to be conducted under a gas flow containing oxygen at a concentration of 0.1~10 vol %, and a temperature of 300~500° C. for at least half an hour. The gas flow containing oxygen at a concentration of at least 0.1 vol % enhances the catalytic activity, and an oxygen concentration of 10 vol % or lower increases the selectivity of (meth)acrylic acid. Thermal treatment at a temperature of 300° C. or higher sufficiently activates the catalyst, and treatment at a temperature of 500° C. or lower prevents the structure of the catalyst from collapsing. The oxygen concentration is more preferred to be 1~7 vol %. The temperature of thermal treatment is more preferred to be 360~390° C. The thermal treatment temperature is measured within a range of 1-meter radius from the inlet to introduce a heat medium. The duration of the thermal treatment is preferred to be at least 5 hours but no longer than 50 hours to set the production yield and catalytic activity within an easy control range.

In an embodiment of the present invention, (meth)acrylic acid is produced through gas-phase catalytic oxidation reactions of (meth)acrolein by using molecular oxygen in a fixed-bed reactor configured to have a packed layer containing a packing material and a catalyst layer formed with a catalyst containing molybdenum and vanadium.

The type of a fixed-bed reactor used in the method related to the present invention is not limited to any specific type; for example, multitubular heat exchangers, single-tubular heat exchangers, autothermic reactors, adiabatic reactors, multi-stage adiabatic reactors and the like may be used. For industrial purposes, fixed-bed multitubular heat exchanges are preferred.

A fixed-bed reactor is configured to have a packed layer and a catalyst layer. For example, a fixed-bed reactor includes a reaction tube where a packed layer and a catalyst layer are formed. A source gas containing (meth)acrolein and molecular oxygen is supplied from the packed-layer side so that the gas-phase catalytic oxidation reactions of (meth) acrolein are carried out. The packed layer and catalyst layer are preferred to make contact with each other. The length of the packed layer is not limited specifically as long as the reaction gas is sufficiently cooled or preheated. For example, it is set at 100~1000 mm. Alternatively, it is an option for a fixed-bed reactor configured to have a mixed layer formed with a mixture of a packing material and a catalyst between the packed layer and catalyst layer so as to avoid hotspot phenomena during oxidation reactions as well as to improve the selectivity and life of the catalyst. It is another option for a fixed-bed reactor configured to have an outlet layer containing a packing material on the outlet side so as to suppress sequential reactions by shortening the time for the gas to stay in an empty space. The length of an outlet layer is not limited specifically as long as the reaction gas is sufficiently preheated; for example, it may be 10~1000 mm.

The concentration of (meth)acrolein in a source gas is not limited specifically, but it is preferred to be 1~20 vol %, more preferably 3~10 vol %, In addition, at the initial stage of reactions, the concentration of (meth)acrolein in the source gas may be increased incrementally so as to raise the reaction load in stages. Furthermore, (meth)acrolein may include a trace amount of impurities such as water and lower saturated aldehyde. Such impurities do not have any substantial impact on reactions.

It is cost effective to use air as an oxygen source. However, it is an option to use air enriched with pure oxygen if applicable. The oxygen concentration of a source gas is preferred to have a molar ratio of 0.3~4, more preferably 0.4~2.5. A source gas may be diluted by adding moisture vapor and inert gases such as nitrogen and carbon dioxide. Such inert gases may be used as a carrier gas when (meth) acrolein is vaporized. The (meth)acrolein, oxygen-containing gas and inert gas may be supplied separately to the reactor, or may be mixed together prior to being fed into the reactor.

The reaction pressure is preferred to be from atmospheric pressure to multi-atmospheric pressure, more preferably 20~200 kPa. The reaction temperature is preferred to be 230~450° C., more preferably 250~400° C., even more preferably 250~350° C.

EXAMPLES

In the following, the present invention is described in further detail with reference to examples and comparative examples. However, the present invention is not limited to those below. In the descriptions, "part" indicates "part by mass."

In the examples and comparative examples, the reaction rate of methacrolein, the selectivity of produced methacrylic acid, the yield of the methacrylic acid are calculated by formulas (2)-(4) below.

Reaction rate of methacrolein [%]=$A/B$×100 (2)

Selectivity of methacrylic acid [%]=$C/A$×100 (3)

Yield of methacrylic acid [%]=$C/B$×100 (4)

Here, "A" indicates the number of moles of reacted methacrolein, "B" indicates the number of moles of supplied methacrolein, and "C" indicates the number of moles of produced methacrylic acid. Gas chromatography was employed for analysis.

The mass of a catalyst in a packed layer, namely, the rate of contained catalyst to the total mass of the packing material in the packed layer, was obtained by formula (5) below.

Rate of contained catalyst [mass %]=$E/D$×100 (5)

Here, "D" indicates the total mass of the packing material in a packed layer. "E" indicates the mass of the catalyst contained in the packed layer, which is the total mass of the catalyst attached to the packing material and the catalyst located in the gaps of the packing material in the packed layer.

A pair of scales with a minimum scale value of 0.1 mg was used to measure mass.

Example 1

Into 400 parts of pure water, 100 parts of molybdenum trioxide, 5.4 parts of ammonium metavanadate, 10.0 parts of 85 mass % phosphoric acid solution, 2.5 parts of antimony trioxide, and 1.4 parts of copper (II) nitrate trihydrate were dissolved. The resultant solution was heated to 95° C. while being stirred, and the solution was stirred for 180 minutes at a constant temperature of 95° C. Next, after cooling the solution to 50° C., 2.7 parts of 60 mass % arsenic-acid solution were added and 4.5 parts of cesium nitrate dissolved in 20 parts of pure water were further added. Then, 2.3 parts of potassium hydroxide dissolved in 20 parts of pure water were dripped into the solution that was kept at a temperature of 70° C., and 25.3 parts of 25 mass % ammonia water were added. In addition, 8.5 parts of bismuth nitrate dissolved into 3.0 parts of pure water and 5.0 parts of cerium nitrate dissolved into 3.0 parts of pure water were dripped respectively into the solution, and the solution was stirred for 15 minutes. The obtained slurry containing a catalyst material was dried. Accordingly, powdered catalyst with an average particle diameter of 30 μm was achieved. The elemental composition of the powdered catalyst excluding oxygen was $P_{1.5}Mo_{12}V_{0.8}Cu_{0.1}K_{0.7}Cs_{0.4}Bi_{0.3}Sb_{0.3}Ce_{0.2}As_{0.2}$. The elemental composition was obtained by using the initial amounts of materials fed into the solution. After 97000 grams of the powdered catalyst were mixed well with 3000 grams of graphite powder, the mixture was molded into 4-mm-high columnar pellet with a 4-mm diameter. Solid catalyst (Z1) containing 3 mass % of graphite was obtained to be used for gas-phase catalytic oxidation reactions of methacrolein.

Next, a fixed-bed reactor configured to have a 6-m-long stainless-steel reaction tube with a 3-cm diameter was prepared. After the reaction tube was washed with water to completely remove deposits and was then dried, 250.8063 grams of 7-mm outer diameter unused ceramic balls were dropped into the reaction tube at a packing density of 1.25 kg/L to form a packed layer. Then, 3500 grams of solid catalyst (Z1) were packed to form a catalyst layer. Moreover, the unused ceramic balls were packed in the upper space of the reaction tube to form an outlet layer.

Next, a heat medium bath to heat the reaction tube was heated to 380° C. at a rate of 25° C./hr, and kept at 380° C. for 12 hours to calcine solid catalyst (Z1). Air was fed from the top of the reaction tube at a rate of 1000 NL/hr from the start of heating and while the temperature was kept at 380° C.

Next, the temperature of the heat medium bath was set at 290° C., and 3000 NL/hr of a mixed gas containing 5 vol % of methacrolein, 12 vol % of oxygen, 10 vol % of moisture vapor and 73 vol % of nitrogen was fed from the bottom of the reaction tube to carry out gas-phase catalytic oxidation reactions of methacrolein for 240 hours. The gauge pressure at the inlet to the reaction tube was 110 kPa.

Next, the content was removed from the reaction tube by dividing it into the packed layer and part of the catalyst layer on one hand and the outlet layer and the remaining catalyst layer on the other hand, so that the ceramic balls in the packed layer and outlet layer would not be mixed. The ceramic balls of the removed packed layer and removed catalyst were put through a sieve to separate them, and ceramic balls (Y1) with attached catalyst were obtained. The mass of (Y1) was 259.6096 grams. Then, (Y1) was cleaned for 30 minutes in running DI water and air dried. Accordingly, 251.0563 grams of cleaned ceramic balls (X1) were obtained.

Next, the reaction tube was cleaned well using DI water and a brush to completely remove deposits and was then dried. Then, 251.0563 grams of cleaned ceramic balls (X1) were packed to form a packed layer. The rate of contained catalyst was 0.100 mass %. Then, 1600 grams of unused solid catalyst (Z1) and 400 grams of unused ceramic balls were mixed evenly and a mixed layer was formed by packing the obtained mixture while preventing the catalyst from being powdered. In addition, 1900 grams of unused solid catalyst (Z1) were packed to form a catalyst layer. Moreover, unused ceramic balls were packed into the remaining space in the reaction tube to form an outlet layer.

Next, solid catalyst (Z1) was calcined under the same conditions as above. Then, the temperature of the heat medium bath was set at 290° C., and 3000 NL/hr of a mixed gas containing 5 vol % of methacrolein, 12 vol % of oxygen, 10 vol % of moisture vapor and 73 vol % of nitrogen was fed from the bottom of the reaction tube to carry out gas-phase catalytic oxidation reactions of methacrolein. The gauge pressure at the inlet to the reaction tube was 110 kPa. When the reaction product 24 hours after the start of reactions was analyzed, the reaction rate of methacrolein was 78.5%, the selectivity of methacrylic acid was 78.3%, the yield of methacrylic acid was 61.5%, and the differential pressure between the inlet pressure and outlet pressure of the reaction tube (hereinafter referred to as the differential pressure) was 35 kPa.

Next, while the temperature of the heat medium bath was controlled so that the reaction rate of methacrolein was kept at 78%, continuous testing was conducted until the temperature of the heat medium bath reached 300° C. The duration of continuous operation was 8712 hours. When the temperature of the heat medium bath reached 300° C., the reaction rate of methacrolein was 78.3%, the selectivity of methacrylic acid was 80.6%, the yield of methacrylic acid was 63.1%, and the differential pressure was 35 kPa.

Next, after the reactions were stopped and the tube was cooled, the catalyst and ceramic balls in the reaction tube were removed from the bottom of the tube. Then, to measure the amount of carbides, 50 grams of the lowermost layer of the removed used catalyst were analyzed by organic elemental analysis so that the total amount of carbon in the catalyst was measured. To perform organic elemental analysis, an automatic elemental analyzer (brand name: EA 1110 CHNS—O, made by Amco Inc.) was used. The amount of carbon in the catalyst was found to be 3.015 mass %. In addition, the catalyst or the like attached to the surface of the reaction tube around where 50 grams of the lowermost layer were located was shaved using a brush, and the total amount of carbon was measured the same as above. The amount of carbon in the catalyst and the like attached to the tube surface was found to be 3.083 mass %.

Example 2

The reaction tube used in Example 1 was cleaned well using DI water and a brush to completely remove deposits and was then dried. Then, 250.7029 grams of the above unused ceramic balls were packed to form a packed layer. Also, 3500 grams of solid catalyst (Z1) were packed to form a catalyst layer while preventing the catalyst from being powdered. In addition, the above unused ceramic balls were packed into the remaining upper space in the reaction tube to form an outlet layer. After that, the catalyst was calcined under the same conditions as in Example 1, and the gas-phase catalytic oxidation reactions of methacrolein were carried out under the same conditions as in Example 1.

Next, the content was removed from the reaction tube by dividing it into the packed layer and part of the catalyst layer on one hand and the outlet layer and the remaining catalyst layer on the other hand, so that the ceramic balls in the packed layer and outlet layer would not be mixed. The ceramic balls of the removed packed layer and removed catalyst were put through a sieve to separate them, and ceramic balls (Y2) with attached catalyst were obtained. The mass of (Y2) was 260.8313 grams. Then, (Y2) was cleaned for 60 minutes in running DI water and air dried. Accordingly, 250.8046 grams of cleaned ceramic balls (X2) were obtained.

Next, the reaction tube was cleaned well using DI water and a brush to completely remove deposits and was then dried. Then, 250.8046 grams of cleaned ceramic balls (X2) were packed to form a packed layer. The rate of contained catalyst was 0.041 mass %, Then, 1600 grams of unused solid catalyst (Z1) and 400 grams of the above unused ceramic balls were mixed evenly and a mixed layer was formed by packing the obtained mixture while preventing the catalyst from being powdered. In addition, 1900 grams of unused solid catalyst (Z1) were packed to form a catalyst layer. Moreover, the above unused ceramic balls were packed into the remaining space in the reaction tube to form an outlet layer.

Next, the catalyst was calcined under the same conditions as above, and the gas-phase catalytic oxidation reactions of methacrolein were carried out under the same conditions as in Example 1. The gauge pressure at the inlet to the reaction tube was 110 kPa. When the reaction product 24 hours after the start of reactions was analyzed, the reaction rate of methacrolein was 78.6%, the selectivity of methacrylic acid was 78.3%, the yield of methacrylic acid was 61.5%, and the differential pressure was 35 kPa.

Next, continuous testing was conducted the same as in Example 1. The duration of continuous operation was 8880 hours. When the temperature of the heat medium bath reached 300° C., the reaction rate of methacrolein was 78.5%, the selectivity of methacrylic acid was 80.5%, the yield of methacrylic acid was 63.2%, and the differential pressure was 35 kPa.

Next, after the reactions were stopped and the tube was cooled, the catalyst and ceramic balls in the reaction tube were removed from the bottom of the tube. Then, the total amount of carbon in the catalyst was measured the same as in Example 1. The amount of carbon in the catalyst was found to be 3.079 mass %. In addition, the catalyst or the like attached to the surface of the reaction tube around where 50 grams of the lowermost layer were located was shaved using a brush, and the total amount of carbon was measured the same as above. The amount of carbon in the catalyst and the like attached to the tube surface was found to be 3.054 mass %.

Example 3

The reaction tube used in Example 2 was cleaned well using DI water and a brush to completely remove deposits and was then dried. Then, 250.3238 grams of the above unused ceramic balls were packed to form a packed layer. Also, 3500 grams of solid catalyst (Z1) were packed to form a catalyst layer while preventing the catalyst from being powdered. In addition, the above unused ceramic balls were packed into the remaining upper space in the reaction tube to form an outlet layer. After that, the catalyst was calcined under the same conditions as in Example 1, and the gas-phase catalytic oxidation reactions of methacrolein were carried out under the same conditions as in Example 1.

Next, the content was removed from the reaction tube by dividing it into the packed layer and part of the catalyst layer on one hand and the outlet layer and the remaining catalyst layer on the other hand, so that the ceramic balls in the packed layer and outlet layer would not be mixed. The ceramic balls of the removed packed layer and removed catalyst were put through a sieve to separate them, and ceramic balls (Y3) with attached catalyst were obtained. The mass of (Y3) was 261.3986 grams. Then, (Y3) was soaked in 1 mass % ammonia water for 60 minutes, cleaned for 30 minutes in running DI water and air dried. Accordingly, 250.3421 grams of cleaned ceramic balls (X3) were obtained.

Next, the reaction tube was cleaned well using DI water and a brush to completely remove deposits and was then dried. Then, 250.3421 grams of cleaned ceramic balls (X3) were packed to form a packed layer. The rate of contained catalyst was 0.007 mass %. Then, 1600 grams of unused solid catalyst (Z1) and 400 grams of the above unused ceramic balls were mixed evenly and a mixed layer was formed by packing the obtained mixture while preventing the catalyst from being powdered, in addition, 1900 grams of unused solid catalyst (Z 1) were packed to form a catalyst layer. Moreover, the above unused ceramic balls were packed into the remaining space in the reaction tube to form an outlet layer.

Next, the catalyst was calcined under the same conditions as above, and the gas-phase catalytic oxidation reactions of methacrolein were carried out under the same conditions as in Example 1. The gauge pressure at the inlet to the reaction tube was 110 kPa. When the reaction product 24 hours after the start of reactions was analyzed, the reaction rate of methacrolein was 78.4%, the selectivity of methacrylic acid was 78.6%, the yield of methacrylic acid was 61.6%, and the differential pressure was 35 kPa.

Next, continuous testing was conducted the same as in Example 1. The duration of continuous operation was 8784 hours. When the temperature of the heat medium bath reached 300° C., the reaction rate of methacrolein was 78.7%, the selectivity of methacrylic acid was 80.4%, the yield of methacrylic acid was 63.3%, and the differential pressure was 35 kPa.

Next, after the reactions were stopped and the tube was cooled, the catalyst and ceramic balls in the reaction tube were removed from the bottom of the tube. Then, the total amount of carbon in the catalyst was measured the same as in Example 1. The amount of carbon in the catalyst was found to be 3.023 mass %, In addition, the catalyst or the like attached to the surface of the reaction tube around where 50 grams of the lowermost layer were located was shaved using a brush, and the total amount of carbon was measured the same as above. The amount of carbon in the catalyst and the like attached to the tube surface was found to be 3.012 mass %.

Example 4

The reaction tube used in Example 3 was cleaned well using DI water and a brush to completely remove deposits and was then dried. Then, 250.7172 grams of the above unused ceramic balls were packed to form a packed layer. Also, 3500 grams of solid catalyst (Z1) were packed to form a catalyst layer while preventing the catalyst from being powdered. In addition, the above unused ceramic balls were packed into the remaining upper space in the reaction tube to form an outlet layer. After that, the catalyst was calcined under the same conditions as in Example 1, and the gas-phase catalytic oxidation reactions of methacrolein were carried out under the same conditions as in Example 1.

Next, the content was removed from the reaction tube by dividing it into the packed layer and part of the catalyst layer on one hand and the outlet layer and the remaining catalyst layer on the other hand, so that the ceramic balls in the packed layer and outlet layer would not be mixed. The ceramic balls of the removed packed layer and removed catalyst were put through a sieve to separate them, and ceramic balls (Y4) with attached catalyst were obtained. The mass of (Y4) was 259.4105 grams. Then, the catalyst attached on (Y4) was removed by using a metallic brush, and 250.9629 grams of polished ceramic balls (X4) were obtained.

Next, the reaction tube was cleaned well using DI water and a brush to completely remove deposits and was then dried. Then, 250.9629 grams of polished ceramic balls (X4) were packed to form a packed layer. The rate of contained catalyst was 0.098 mass %. Then, 1600 grams of unused solid catalyst (Z1) and 400 grams of the above unused ceramic balls were mixed evenly and a mixed layer was formed by packing the obtained mixture while preventing the catalyst from being powdered. In addition, 1900 grams of unused solid catalyst (Z1) were packed to form a catalyst layer. Moreover, the above unused ceramic balls were packed into the remaining space in the reaction tube to form an outlet layer.

Next, the catalyst was calcined under the same conditions as above, and the gas-phase catalytic oxidation reactions of methacrolein were carried out under the same conditions as in Example 1. The gauge pressure at the inlet to the reaction tube was 110 kPa. When the reaction product 24 hours after the start of reactions was analyzed, the reaction rate of methacrolein was 78.4%, the selectivity of methacrylic acid was 78.6%, the yield of methacrylic acid was 61.6%, and the differential pressure was 35 kPa.

Next, continuous testing was conducted the same as in Example 1. The duration of continuous operation was 8832 hours. When the temperature of the heat medium bath reached 300° C., the reaction rate of methacrolein was 78.2%, the selectivity of methacrylic acid was 80.7%, the yield of methacrylic acid was 63.1%, and the differential pressure was 35 kPa.

Next, after the reactions were stopped and the tube was cooled, the catalyst and ceramic balls in the reaction tube were removed from the bottom of the tube. Then, the total amount of carbon in the catalyst was measured the same as in Example 1. The amount of carbon in the catalyst was found to be 3.163 mass %. In addition, the catalyst or the like attached to the surface of the reaction tube around where 50 grams of the lowermost layer were located was shaved using a brush, and the total amount of carbon was measured the same as above. The amount of carbon in the catalyst and the like attached to the tube surface was found to be 3.268 mass %.

Example 5

The reaction tube used in Example 4 was cleaned well using DI water and a brush to completely remove deposits and was then dried. Then, 150.6190 grams of the above unused ceramic balls were packed to form a packed layer. Also, 3500 grams of solid catalyst (Z1) were packed to form a catalyst layer while preventing the catalyst from being powdered. In addition, the above unused ceramic balls were packed into the remaining upper space in the reaction tube to form an outlet layer. After that, the catalyst was calcined under the same conditions as in Example 1, and the gas-phase catalytic oxidation reactions of methacrolein were carried out under the same conditions as in Example 1.

Next, the content was removed from the reaction tube by dividing it into the packed layer and part of the catalyst layer on one hand and the outlet layer and the remaining catalyst layer on the other hand, so that the ceramic balls in the packed layer and outlet layer would not be mixed. The ceramic balls of the removed packed layer and removed catalyst were put through a sieve to separate them, and ceramic balls (Y5) with attached catalyst were obtained. The mass of (Y5) was 155.2692 grams. Then, (Y5) was cleaned for 40 minutes in running DI water and was then air dried. Accordingly, 150.7197 grams of cleaned ceramic balls (X5) were obtained.

Next, the reaction tube was cleaned well using DI water and a brush to completely remove deposits and was then dried. Then, 100.2596 grams of the above unused ceramic balls and cleaned ceramic balls (X5) were mixed well and 250.9793 grams of the mixed ceramic balls were packed to form a packed layer. The rate of contained catalyst was 0.040 mass %. Then, 1600 grams of unused solid catalyst (Z1) and 400 grams of the above unused ceramic balls were mixed evenly and a mixed layer was formed by packing the obtained mixture while preventing the catalyst from being powdered. In addition, 1900 grams of unused solid catalyst (Z1) were packed to form a catalyst layer. Moreover, the above unused ceramic balls were packed into the remaining space in the reaction tube to form an outlet layer.

Next, the catalyst was calcined under the same conditions as above, and the gas-phase catalytic oxidation reactions of methacrolein were carried out under the same conditions as in Example 1. The gauge pressure at the inlet to the reaction tube was 110 kPa. When the reaction product 24 hours after the start of reactions was analyzed, the reaction rate of methacrolein was 78.6%, the selectivity of methacrylic acid was 78.3%, the yield of methacrylic acid was 61.5%, and the differential pressure was 35 kPa.

Next, continuous testing was conducted the same as in Example 1. The duration of continuous operation was 8712 hours. When the temperature of the heat medium bath reached 300° C., the reaction rate of methacrolein was 78.5%, the selectivity of methacrylic acid was 80.5%, the yield of methacrylic acid was 63.2%, and the differential pressure was 35 kPa.

Next, after the reactions were stopped and the tube was cooled, the catalyst and ceramic balls in the reaction tube were removed from the bottom of the tube. Then, the total amount of carbon in the catalyst was measured the same as in Example 1. The amount of carbon in the catalyst was found to be 3.028 mass %. In addition, the catalyst or the like attached to the surface of the reaction tube around where 50 grams of the lowermost layer were located was shaved using a brush, and the total amount of carbon was measured the same as above. The amount of carbon in the catalyst and the like attached to the tube surface was found to be 3.119 mass %.

Example 6

The reaction tube used in Example 5 was cleaned well using DI water and a brush to completely remove deposits and was then dried. Then, 250.6282 grams of 6-mm-high unused SUS cod springs with a 6-mm diameter were packed to form a packed layer. Also, 3500 grams of solid catalyst (Z1) were packed to form a catalyst layer while preventing the catalyst from being powdered. In addition, the above unused ceramic balls were packed into the remaining upper space in the reaction tube to form an outlet layer. After that, the catalyst was calcined under the same conditions as in Example 1, and the gas-phase catalytic oxidation reactions of methacrolein were carried out under the same conditions as in Example 1.

Next, the content was removed from the reaction tube by dividing it into the packed layer and part of the catalyst layer on one hand and the outlet layer and the remaining catalyst layer on the other hand, so that the SUS coil springs in the packed layer and ceramic balls in the outlet layer would not be mixed. The SUS coil springs of the removed packed layer and removed catalyst were put through a sieve to separate them, and SUS coil springs (Y6) with attached catalyst were obtained. The mass of (Y6) was 261.3986 grams. Then, (Y6) was soaked in 1 mass % ammonia water for 36 hours and cleaned for 30 minutes in running DI water and was then air dried. Accordingly, 250.6319 grams of cleaned SUS coil springs (X6) were obtained.

Next, the reaction tube was cleaned well using DI water and a brush to completely remove deposits and was then dried. Then, 250.6319 grams of cleaned SUS coil springs (X6) were packed to form a packed layer. The rate of contained catalyst was 0.001 mass %. Then, 1600 grams of unused solid catalyst (Z1) and 400 grams of the above unused SUS coil springs were mixed evenly and a mixed layer was formed by packing the obtained mixture while preventing the catalyst from being powdered. In addition, 1900 grams of unused solid catalyst (Z1) were packed to form a catalyst layer. Moreover, the above unused ceramic balls were packed into the remaining space in the reaction tube to form an outlet layer.

Next, the catalyst was calcined under the same conditions as above, and the gas-phase catalytic oxidation reactions of methacrolein were carried out under the same conditions as in Example 1. The gauge pressure at the inlet to the reaction tube was 110 kPa. When the reaction product 24 hours after the start of reactions was analyzed, the reaction rate of methacrolein was 78.5%, the selectivity of methacrylic acid was 78.5%, the yield of methacrylic acid was 61.6%, and the differential pressure was 35 kPa.

Next, continuous testing was conducted the same as in Example 1. The duration of continuous operation was 8880 hours. When the temperature of the heat medium bath reached 300° C., the reaction rate of methacrolein was 78.6%, the selectivity of methacrylic acid was 80.4%, the yield of methacrylic acid was 63.2%, and the differential pressure was 35 kPa.

Next, after the reactions were stopped and the tube was cooled, the catalyst and ceramic balls in the reaction tube were removed from the bottom of the tube. Then, the total amount of carbon in the catalyst was measured the same as in Example 1. The amount of carbon in the catalyst was found to be 3.014 mass %. In addition, the catalyst or the like attached to the surface of the reaction tube around where 50 grams of the lowermost layer were located was shaved using a brush, and the total amount of carbon was measured the same as above. The amount of carbon in the catalyst and the like attached to the tube surface was found to be 3.019 mass %.

Comparative Example 1

The reaction tube used in Example 6 was cleaned well using DI water and a brush to completely remove deposits and was then dried. Then, 250.4472 grams of the above unused ceramic balls were packed to form a packed layer. Also, 3500 grams of solid catalyst (Z1) were packed to form a catalyst layer while preventing the catalyst from being powdered. In addition, the above unused ceramic balls were packed into the remaining upper space in the reaction tube to form an outlet layer. After that, the catalyst was calcined under the same conditions as in Example 1, and the gas-phase catalytic oxidation reactions of methacrolein were carried out under the same conditions as in Example 1.

Next, the content was removed from the reaction tube by dividing it into the packed layer and part of the catalyst layer on one hand and the outlet layer and the remaining catalyst layer on the other hand, so that the ceramic balls in the packed layer and outlet layer would not be mixed. The ceramic balls of the removed packed layer and removed catalyst were put through a sieve to separate them, and ceramic balls (Y7) with attached catalyst were obtained. The mass of (Y7) was 260.3894 grams.

Next, the reaction tube was cleaned well using DI water and a brush to completely remove deposits and was then dried. Then, 260.3894 grams of ceramic balls (Y7) with attached catalyst were packed to form a packed layer. The rate of contained catalyst was 3.970 mass %. Then, 1600 grams of unused solid catalyst (Z1) and 400 grams of the above unused ceramic balls were mixed evenly and a mixed layer was formed by packing the obtained mixture while preventing the catalyst from being powdered. In addition, 1900 grams of unused solid catalyst (Z1) were packed to form a catalyst layer. Moreover, the above unused ceramic balls were packed into the remaining space in the reaction tube to form an outlet layer.

Next, the catalyst was calcined under the same conditions as above, and the gas-phase catalytic oxidation reactions of methacrolein were carried out under the same conditions as in Example 1. The gauge pressure at the inlet to the reaction tube was 110 kPa. When the reaction product 24 hours after the start of reactions was analyzed, the reaction rate of methacrolein was 78.6%, the selectivity of methacrylic acid was 78.4%, the yield of methacrylic acid was 61.6%, and the differential pressure was 35 kPa.

Next, continuous testing was conducted the same as in Example 1. The continuous testing duration was 7800 hours. When the temperature of the heat medium bath reached 300° C., the reaction rate of methacrolein was 78.6%, the selectivity of methacrylic acid was 79.1%, the yield of methacrylic acid was 62.2%, and the differential pressure was 37 kPa. The differential pressure was up 5.7%.

Next, after the reactions were stopped and the tube was cooled, the catalyst and ceramic balls in the reaction tube were removed from the bottom of the tube. Then, the total amount of carbon in the catalyst was measured the same as in Example 1. The amount of carbon in the catalyst was found to be 5.592 mass %. In addition, the catalyst or the like attached to the surface of the reaction tube around where 50 grams of the lowermost layer were located was shaved using a brush, and the total amount of carbon was measured the same as above. The amount of carbon in the catalyst and the like attached to the tube surface was found to be 5.673 mass %.

Comparative Example 2

The reaction tube used in Comparative Example 1 was cleaned well using DI water and a brush to completely remove deposits and was then dried. Then, 250.8957 grams of the above unused ceramic balls were packed to form a packed layer. Also, 3500 grams of solid catalyst (Z1) were packed to form a catalyst layer while preventing the catalyst from being powdered. In addition, the above unused ceramic balls were packed into the remaining upper space in the reaction tube to form an outlet layer. After that, the catalyst was calcined under the same conditions as in Example 1, and the gas-phase catalytic oxidation reactions of methacrolein were carried out under the same conditions as in Example 1.

Next, the content was removed from the reaction tube by dividing it into the packed layer and part of the catalyst layer on one hand and the outlet layer and the remaining catalyst layer on the other hand, so that the ceramic balls in the packed layer and outlet layer would not be mixed. The ceramic balls of the removed packed layer and removed catalyst were put through a sieve to separate them, and ceramic balls (Y8) with attached catalyst were obtained. The mass of (Y8) was 261.2988 grams. Then, (Y8) was cleaned for 10 minutes in running DI water and air dried. Accordingly, 251.3977 grams of cleaned ceramic balls (X7) were obtained.

Next, the reaction tube was cleaned well using DI water and a brush to completely remove deposits and was then dried. Then, 251.3239 grams of cleaned ceramic balls (X7) were packed to form a packed layer. The rate of contained catalyst was 0.200 mass %. Then, 1600 grams of unused solid catalyst (Z1) and 400 grams of the above unused ceramic balls were mixed evenly and a mixed layer was formed by packing the obtained mixture while preventing the catalyst from being powdered. In addition, 1900 grams of unused solid catalyst (Z1) were packed to form a catalyst layer. Moreover, the above unused ceramic balls were packed into the remaining space in the reaction tube to form an outlet layer.

Next, the catalyst was calcined under the same conditions as above, and the gas-phase catalytic oxidation reactions of methacrolein were carried out under the same conditions as in Example 1, The gauge pressure at the inlet to the reaction tube was 110 kPa. When the reaction product 24 hours after the start of reactions was analyzed, the reaction rate of methacrolein was 78.6%, the selectivity of methacrylic acid was 78.2%, the yield of methacrylic acid was 61.5%, and the differential pressure was 35 kPa.

Next, continuous testing was conducted the same as in Example 1. The duration of continuous operation was 7944 hours. When the temperature of the heat medium bath reached 300° C., the reaction rate of methacrolein was 78.3%, the selectivity of methacrylic acid was 79.7%, the yield of methacrylic acid was 62.4%, and the differential pressure was 37 kPa. The differential pressure was up 5.7%.

Next, after the reactions were stopped and the tube was cooled, the catalyst and ceramic balls in the reaction tube were removed from the bottom of the tube. Then, the total amount of carbon in the catalyst was measured the same as in Example 1. The amount of carbon in the catalyst was found to be 4.192 mass %. In addition, the catalyst or the like attached to the surface of the reaction tube around where 50 grams of the lowermost layer were located was shaved using a brush, and the total amount of carbon was measured the same as above. The amount of carbon in the catalyst and the like attached to the tube surface was found to be 4.272 mass %.

Comparative Example 3

The reaction tube used in Comparative Example 2 was cleaned well using DI water and a brush to completely remove deposits and was then dried. Then, 250.6139 grams of the above unused SUS coil springs were packed to form a packed layer. Also, 3500 grams of solid catalyst (Z1) were packed to form a catalyst layer while preventing the catalyst from being powdered. In addition, the above unused ceramic balls were packed into the remaining upper space in the reaction tube to form an outlet layer. After that, the catalyst was calcined under the same conditions as in Example 1, and the gas-phase catalytic oxidation reactions of methacrolein were carried out under the same conditions as in Example 1.

Next, the content was removed from the reaction tube by dividing it into the packed layer and part of the catalyst layer on one hand and the outlet layer and the remaining catalyst layer on the other hand, so that the SUS coil springs in the packed layer and ceramic balls in the outlet layer would not be mixed. The SUS coil springs of the removed packed layer and removed catalyst were put through a sieve to separate them, and SUS coil springs (Y9) with attached catalyst were obtained. The mass of (Y9) was 263.9713 grams.

Next, the reaction tube was cleaned well using DI water and a brush to completely remove deposits and was then dried. Then, 263.9713 grams of SUS coil springs (Y9) with attached catalyst were packed to form a packed layer. The rate of contained catalyst was 5.320 mass %. Then, 1600 grams of unused solid catalyst (Z1) and 400 grams of the above unused SUS coil springs were mixed evenly and a mixed layer was formed by packing the obtained mixture while preventing the catalyst from being powdered. In addition, 1900 grams of unused solid catalyst (Z1) were packed to form a catalyst layer. Moreover, the above unused ceramic balls were packed into the remaining space in the reaction tube to form an outlet layer.

Next, the catalyst was calcined under the same conditions as above, and the gas-phase catalytic oxidation reactions of methacrolein were carried out under the same conditions as in Example 1. The gauge pressure at the inlet to the reaction tube was 110 kPa. When the reaction product 24 hours after the start of reactions was analyzed, the reaction rate of methacrolein was 78.3%, the selectivity of methacrylic acid was 78.6%, the yield of methacrylic acid was 61.5%, and the differential pressure was 36 kPa.

Next, continuous testing was conducted the same as in Example 1. The duration of continuous operation was 7728 hours. When the temperature of the heat medium bath reached 300° C., the reaction rate of methacrolein was 78.4%, the selectivity of methacrylic acid was 79.0%, the yield of methacrylic acid was 61.9%, and the differential pressure was 39 kPa. The differential pressure was up 8.3%.

Next, after the reactions were stopped and the tube was cooled, the catalyst and ceramic balls in the reaction tube were removed from the bottom of the tube. Then, the total amount of carbon in the catalyst was measured the same as in Example 1. The amount of carbon in the catalyst was found to be 6.731 mass %. In addition, the catalyst or the like attached to the surface of the reaction tube around where 50 grams of the lowermost layer were located was shaved using a brush, and the total amount of carbon was measured the same as above. The amount of carbon in the catalyst and the like attached to the tube surface was found to be 6.758 mass %.

Comparative Example 4

The reaction tube used in Comparative Example 3 was cleaned well using DI water and a brush to completely remove deposits and was then dried. Then, 150.3387 grams of the above unused ceramic balls were packed to form a packed layer. Also, 3500 grams of solid catalyst (Z1) were packed to form a catalyst layer while preventing the catalyst from being powdered. In addition, the above unused ceramic balls were packed into the remaining upper space in the reaction tube to form an outlet layer. After that, the catalyst was calcined under the same conditions as in Example 1, and the gas-phase catalytic oxidation reactions of methacrolein were carried out under the same conditions as in Example 1.

Next, the content was removed from the reaction tube by dividing it into the packed layer and part of the catalyst layer on one hand and the outlet layer and the remaining catalyst layer on the other hand, so that the ceramic balls in the packed layer and outlet layer would not be mixed. The ceramic balls of the removed packed layer and removed catalyst were put through a sieve to separate them, and ceramic balls (Y10) with attached catalyst were obtained. The mass of (Y10) was 156.7213 grams.

Next, the reaction tube was cleaned well using DI water and a brush to completely remove deposits and was then dried. Then, 100.8122 grams of the above unused ceramic balls and ceramic balls (Y10) with attached catalyst were mixed well and 257.5335 grams of the mixture were packed to form a packed layer. The rate of contained catalyst was 2.541 mass %. Then, 1600 grams of unused solid catalyst (Z1) and 400 grams of the above unused ceramic balls were mixed evenly and a mixed layer was formed by packing the obtained mixture while preventing the catalyst from being powdered. In addition, 1900 grams of unused solid catalyst (Z1) were packed to form a catalyst layer. Moreover, the above unused ceramic balls were packed into the remaining space in the reaction tube to form an outlet layer.

Next, the catalyst was calcined under the same conditions as above, and the gas-phase catalytic oxidation reactions of methacrolein were carried out under the same conditions as in Example 1. The gauge pressure at the inlet to the reaction tube was 110 kPa. When the reaction product 24 hours after the start of reactions was analyzed, the reaction rate of methacrolein was 78.5%, the selectivity of methacrylic acid was 78.2%, the yield of methacrylic acid was 61.4%, and the differential pressure was 35 kPa.

Next, continuous testing was conducted the same as in Example 1. The duration of continuous operation was 7896 hours. When the temperature of the heat medium bath reached 300° C., the reaction rate of methacrolein was 78.6%, the selectivity of methacrylic acid was 79.3%, the yield of methacrylic acid was 62.3%, and the differential pressure was 37 kPa. The differential pressure was up 5.7%.

Next, after the reactions were stopped and the tube was cooled, the catalyst and ceramic balls in the reaction tube were removed from the bottom of the tube. Then, the total amount of carbon in the catalyst was measured the same as in Example 1. The amount of carbon in the catalyst was found to be 4.649 mass %. In addition, the catalyst or the like attached to the surface of the reaction tube around where 50 grams of the lowermost layer were located was shaved using a brush, and the total amount of carbon was measured the same as above. The amount of carbon in the catalyst and the like attached to the tube surface was found to be 4.775 mass %.

Figure 1:
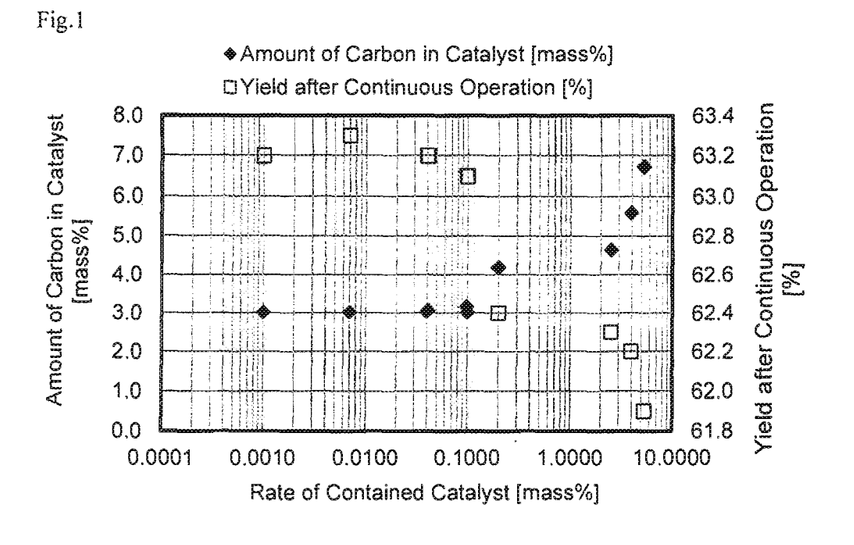
FIG. 1 is a graph showing the results of the examples, indicating relationships among the rate of contained catalyst, the amount of carbon in the catalyst and the yield after continuous operation.
Figure 2:
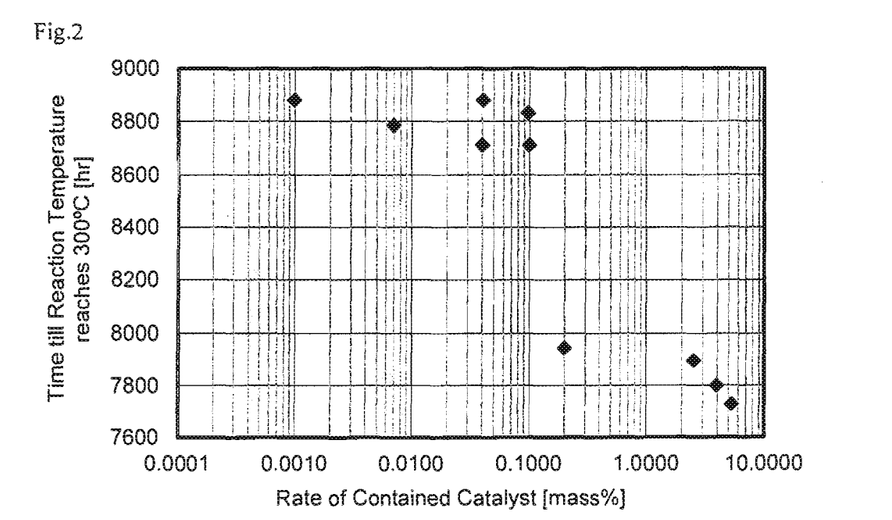
FIG. 2 is a graph showing the results of the examples, indicating relationships between the rate of contained catalyst and the continuous operating time until the reaction temperature reaches 300° C.

The results of Examples 1~6 and Comparative Examples 1~4 are shown in Table 1. Also, FIG. 1 shows relationships among the rate of contained catalyst, the amount of carbon in the catalyst, and the yield after continuous operation. In addition, FIG. 2 shows relationships between the rate of contained catalyst and the duration of continuous operation until the reaction temperature reaches 300° C. By setting the rate of contained catalyst to be 0.001~0.15 mass %, the amount of carbon was substantially the same as that in the graphite used for preparing the catalyst, but the amount of attached carbides during reactions was suppressed. As a result, the production yield of methacrylic acid was enhanced. By contrast, in each of Comparative Examples 1~4 where the rate of contained catalyst exceeded 0.15 mass %, the amount of attached carbides was more than those in the Examples, and the yield of methacrylic acid was lowered.

TABLE 1

| | Packing Material | Rate of Contained Catalyst [mass %] | Cleaning Method | Cleaning Conditions | Yield after 24 hours [%] | Differential Pressure after 24 hours [kPa] | Time till Reaction Temperature reaches 300° C. [hr] | Yield after Continuous Operation [%] | Differential Pressure after Continuous Operation [kPa] | Amount of Carbon in Catalyst [mass %] | Amount of Carbon Attached to Tube [mass %] |
|---|---|---|---|---|---|---|---|---|---|---|---|
| Example 1 | ceramic balls | 0.100 | DI water | 30 min in running water | 61.5 | 35 | 8712 | 63.1 | 35 | 3.015 | 3.083 |
| Example 2 | ceramic balls | 0.041 | DI water | 60 min in running water | 61.5 | 35 | 8880 | 63.2 | 35 | 3.079 | 3.054 |
| Example 3 | ceramic balls | 0.007 | 1% ammonia water + DI water | 60 min soaking + 30 min in running water | 61.6 | 35 | 8784 | 63.3 | 35 | 3.023 | 3.012 |
| Example 4 | ceramic balls | 0.098 | brush polishing | — | 61.6 | 35 | 8832 | 63.1 | 35 | 3.163 | 3.268 |
| Example 5 | ceramic balls | 0.040 | DI water | 40 min in running water | 61.5 | 35 | 8712 | 63.2 | 35 | 3.028 | 3.119 |
| Example 6 | SUS springs | 0.001 | 1% ammonia water + DI water | 30 min soaking + 30 min in running water | 61.6 | 35 | 8880 | 63.2 | 35 | 3.014 | 3.019 |
| Comp. Example 1 | ceramic balls | 3.970 | no cleaning | — | 61.6 | 35 | 7800 | 62.2 | 37 | 5.592 | 5.673 |
| Comp. Example 2 | ceramic balls | 0.200 | DI water | 10 min in running water | 61.5 | 35 | 7944 | 62.4 | 37 | 4.192 | 4.272 |
| Comp. Example 3 | SUS springs | 5.320 | no cleaning | — | 61.5 | 36 | 7728 | 61.9 | 39 | 6.731 | 6.758 |
| Comp. Example 4 | ceramic balls | 2.541 | no cleaning | — | 61.4 | 35 | 7896 | 62.3 | 37 | 4.649 | 4.775 |

The present application is based upon and claims the benefit of priority to Japanese Patent Application No. 2014-093584, filed Apr. 30, 2014. The entire contents of the application are incorporated herein by reference.

The present invention has been described with reference to the embodiments and examples. However, the present invention is not limited to those embodiments and examples. Configuration and details of the present invention, it is possible to make various modifications that can be understood by those skilled in the art within the scope of the present invention.

The invention claimed is:

1. A method for producing (meth)acrylic acid, the method comprising:
   conducting gas-phase catalytic oxidation reactions of (meth)acrolein by using molecular oxygen in a fixed-bed reactor configured to have a packed layer containing a packing material and a catalyst layer formed with a catalyst containing at least molybdenum and vanadium,
   wherein the packed layer contains a packing material that has been used at least once for the gas-phase catalytic oxidation reactions, and
   the catalyst is present in the packed layer at 0.001—0.15 mass % of a total amount of the packing material.

2. The method according to claim 1, wherein the catalyst is present in the packed layer at 0.001—0.1 mass % of the total amount of the packing material.

3. The method according to claim 1, wherein the catalyst is present in the packed layer at 0.001—0.05 mass % of the total amount of the packing material.

4. A method for producing (meth)acrylic acid, the method comprising:
   conducting gas-phase catalytic oxidation reactions of (meth)acrolein by using molecular oxygen in a fixed-bed reactor configured to have a packed layer containing a packing material and a catalyst layer formed with a catalyst containing at least molybdenum and vanadium,
   wherein the packed layer contains a packing material that has been used at least once for above gas-phase catalytic oxidation reactions, and
   the catalyst is attached to the packing material in the packed layer at 0.001—0.15 mass % of a total amount of the packing material in the packed layer.

5. The method according to claim 4, wherein the catalyst is attached to the packing material in the packed layer at 0.001—0.1 mass % of the total amount of the packing material.

6. The method according to claim 4, wherein the catalyst is attached to the packing material in the packed layer at 0.001—0.05 mass % of the total amount of the packing material.

7. The method according to claim 1, wherein the used packing material is what is obtained by cleaning the packing material used at least once for the gas-phase catalytic oxidation reactions.

8. The method according to claim 7, wherein the used packing material is what is obtained after the packing material used at least once for the gas-phase catalytic oxidation reactions is soaked in ammonia water and is then cleaned in deionized water.

9. The method according to claim 1, wherein the packing material is a mixture of the used packing material and an unused packing material.

10. The method according to claim 1, wherein the packing material is at least one type selected from the group consisting of a silica-alumina material and an SUS material.

11. The method according to claim 1, wherein the packing material is shaped in at least one type selected from the group consisting of a spherical material and a coil material.

12. The method according to claim 1, wherein the packing material is at least one type selected from the group consisting of ceramic balls and SUS coil springs.

* * * * *